(12) United States Patent
Jolidon et al.

(10) Patent No.: US 7,951,836 B2
(45) Date of Patent: *May 31, 2011

(54) SUBSTITUTED PHENYL METHANONE DERIVATIVES

(75) Inventors: Synese Jolidon, Blauen (CH); Robert Narquizian, Saint Louis (FR); Roger Norcross, Olsberg (CH); Emmanuel Pinard, Linsdorf (FR)

(73) Assignee: Hoffmann-La Roche Inc., Nutley, NJ (US)

(*) Notice: Subject to any disclaimer, the term of this patent is extended or adjusted under 35 U.S.C. 154(b) by 892 days.

This patent is subject to a terminal disclaimer.

(21) Appl. No.: 11/818,676

(22) Filed: Jun. 15, 2007

(65) Prior Publication Data

US 2007/0299071 A1 Dec. 27, 2007

(30) Foreign Application Priority Data

Jun. 22, 2006 (EP) .................................. 06115916

(51) Int. Cl.
*A61K 31/5355* (2006.01)
*C07D 413/08* (2006.01)
(52) U.S. Cl. ....................... 514/423; 548/531
(58) Field of Classification Search .................. 514/423; 548/531
See application file for complete search history.

(56) References Cited

U.S. PATENT DOCUMENTS

| 7,485,637 B2 | 2/2009 | Jolidon et al. |
| 7,605,163 B2 | 10/2009 | Jolidon et al. |
| 2005/0154024 A1 | 7/2005 | Bryans et al. |

FOREIGN PATENT DOCUMENTS

| WO | WO 2005/014563 | 2/2005 |
| WO | WO 2005/023261 | 3/2005 |
| WO | WO 2006/077026 | 7/2006 |

OTHER PUBLICATIONS

Chabrier et al. "Preparation of N-phhenyl.." CA 136:69731 (2002).*
Praysse et al. "Aminopyrimidines.." CA 147:9933 (2007).*
Tani et al. "Preparation of aryll . . ." CA 138:187795 (2003).*
King "Bioisosteres . . . " Med. Chem. Principle and Practice p. 206-209 (1994).*

* cited by examiner

*Primary Examiner* — Celia Chang
(74) *Attorney, Agent, or Firm* — George W. Johnston; Patricia S. Rocha-Tramaloni; Kimberly J. Prior

(57) ABSTRACT

The present invention relates to compounds of formula I

I

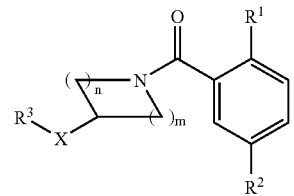

wherein $R^1$, $R^2$, $R^3$, X, n, and m are as defined herein and to pharmaceutically acceptable acid addition salts thereof, to pharmaceutical compositions containing them, and to methods for treating neurological and neuropsychiatric disorders.

22 Claims, No Drawings

SUBSTITUTED PHENYL METHANONE DERIVATIVES

PRIORITY TO RELATED APPLICATION(S)

This application claims the benefit of European Patent Application No. 06115916.6, filed Jun. 22, 2006, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 5(4): 507-518, 2001; Nakazato A and Okuyama S, et al., *Exp. Opin. Ther. Patents*, 10(1): 75-98, 2000). This pharmacological approach poorly address negative and cognitive symptoms which are the redictors of functional outcome (Sharma T., *Br. J. Psychiatry*, 174(suppl. 28): 44-51, 1999).

A complementary model of schizophrenia was proposed in the mid-1960s based upon the psychotomimetic action caused by the blockade of the glutamate system by compounds like phencyclidine (PCP) and related agents (ketamine) which are non-competitive NMDA receptor antagonists. Interestingly, in healthy volunteers, PCP-induced psychotomimetic action incorporates positive and negative symptoms as well as cognitive dysfunction, thus closely resembling schizophrenia in patients (Javitt D C et al., *Biol. Psychiatry*, 45: 668-679, 1999). Furthermore transgenic mice expressing reduced levels of the NMDAR1 subunit display behavioral abnormalities similar to those observed in pharmacologically induced models of schizophrenia, supporting a model in which reduced NMDA receptor activity results in schizophrenia-like behavior (Mohn A R et al., *Cell*, 98: 427-236, 1999).

Glutamate neurotransmission, in particular NMDA receptor activity, plays a critical role in synaptic plasticity, learning and memory, such that NMDA receptors appear to serve as a graded switch for gating the threshold of synaptic plasticity and memory formation (Wiley, N.Y.; Bliss T V and Collingridge G L, *Nature*, 361: 31-39, 1993). Transgenic mice overexpressing the NMDA NR2B subunit exhibit enhanced synaptic plasticity and superior ability in learning and memory (Tang J P et al., *Natur*, 401-63-69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters act by removing neurotransmitters from the extracellular space, and can control their extracellular lifetime and thereby modulate the magnitude of the synaptic transmission (Gainetdinov R R et al, *Trends in Pharm. Sci.*, 23(8): 367-373, 2002).

Glycine transporters) which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., *Mol. Mem. Biol.*, 18: 13-20, 2001). Thus, one strategy to enhance NMDA receptor activity is to elevate the glycine concentration in the local microenvironment of synaptic NMDA receptors by inhibition of GlyT-1 transporter (Bergereon R. et al., *Proc. Natl. Acad. Sci. USA*, 95: 15730-15734, 1998; Chen L. et al., *J. Neurophysiol.*, 89(2): 691-703, 2003).

Glycine transporter inhibitors are suitable for the treatment of neurological and neuropsychiatric disorders. The majority of diseases states implicated are psychoses, schizophrenia (Armer R E and Miller D J, *Exp. Opin. Ther. Patents*, 11 (4): 563-572, 2001), psychotic mood disorders such as severe major depressive disorder, mood disorders associated with psychotic disorders such as acute mania or depression, associated with bipolar disorders and mood disorders, associated with schizophrenia, (Pralong E T et al., *Prog. Neurobiol.*, 67: 173-202, 2002), autistic disorders (Carlsson M L, *J. Neural Trans*, 105: 525-535, 1998), cognitive disorders such as dementias, including age related dementia and senile dementia of the Alzheimer type, memory disorders in a mammal, including a human, attention deficit disorders and pain (Armer R E and Miller D J, *Exp. Opin. Ther. Patents*, 11(4): 563-572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula I

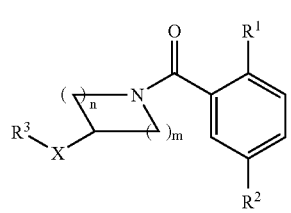

wherein
$R^1$ is —$OR^{1'}$, heterocycloalkyl, aryl or heteroaryl, each of which is unsubstituted or substituted by lower alkyl or halogen;

R¹' is lower alkyl, lower alkyl substituted by halogen, or —(CH₂)ₒ-cycloalkyl;

R² is —S(O)₂-lower alkyl, —S(O)₂NH-lower alkyl, NO₂ or CN;

R³ is aryl or heteroaryl, each of which is unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide;

X is a bond, —CH₂—, —NH—, —CH₂O— or —OCH₂—;

n is 1 or 2;

m is 1 or 2; and o is 0 or 1;

and pharmaceutically acceptable acid addition salts thereof.

Furthermore, the invention includes all racemic mixtures, all their corresponding enantiomers and/or optical isomers.

The present invention also provides pharmaceutical compositions comprising a compound of the invention and a pharmaceutically acceptable carrier and provides processes for the preparation of the compounds and compositions of the invention. Compounds of the invention are good inhibitors of the glycine transporter 1 (GlyT-1), and have good selectivity to glycine transporter 2 (GlyT-2) inhibitors. The invention further provides methods of treating diseases related to activation of NMDA receptors via Glyt-1 inhibition, in particular the treatment of such illnesses as psychoses, dysfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-hydrocarbon chain group containing from 1 to 6 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "cycloalkyl" denotes a saturated carbocyclic ring containing from 3 to 6 carbon atoms.

As used herein, the term "lower alkoxy" denotes a saturated straight- or branched-hydrocarbon chain group containing from 1 to 6 carbon atoms as described above, which is connected via an oxygen atom.

The term "halogen" denotes chlorine, iodine, fluorine and bromine.

The term "aryl" denotes a monovalent carbocyclic aromatic hydrocarbon radical having from 6 to 10 carbon atoms consisting of one or two fused rings in which at least one ring is aromatic in nature, for example phenyl, benzyl, naphthyl or biphenyl.

The term "heteroaryl" denotes a monovalent aromatic carbocyclic radical of one or two fused rings having 6 to 10 ring atoms, which contains at least one heteroatom selected from O, N, and S, for example pyridyl, pyrazinyl, pyrimidinyl, pyridazinyl pyrazolyl, or 1,3,5-triazinyl.

The term "heterocycloalkyl" is synonymous with saturated heterocycle and denotes a saturated non-aromatic hydrocarbon radical of one or two fused rings having 6 to 10 ring atoms, which contains at least one heteroatom selected from O, N, and S, for example oxetanyl, tetrahydrofuranyl, tetrahydropyranyl, azetidinyl, pyrrolidinyl, piperidinyl, piperazinyl, morpholinyl or thiomorpholinyl.

The term "alkyl substituted by halogen" denotes an alkyl group as defined above in which one or more hydrogen atom is replaced with a halogen atom, for example the following groups: CF₃, CHF₂, CH₂F, CH₂CF₃, CH₂CHF₂, CH₂CH₂F, CH₂CH₂CF₃, CH₂CH₂CH₂CF₃, CH₂CH₂Cl, CH₂CF₂CF₃, CH₂CF₂CHF₂, CF₂CHFCF₃, C(CH₃)₂CF₃, CH(CH₃)CF₃ or CH(CH₂F)CH₂F.

The term "alkoxy substituted by halogen" denotes an alkoxy group as defined above in which one or more hydrogen atom is replaced with a halogen atom.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides compounds of formula I

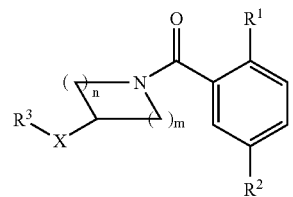

wherein

R¹ is —OR¹', heterocycloalkyl, aryl or heteroaryl, each of which is unsubstituted or substituted by lower alkyl or halogen;

R¹' is lower alkyl, lower alkyl substituted by halogen, or —(CH₂)ₒ-cycloalkyl;

R² is —S(O)₂-lower alkyl, —S(O)₂NH-lower alkyl, NO₂ or CN;

R³ is aryl or heteroaryl, each of which is unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide;

X is a bond, —CH₂—, —NH—, —CH₂O— or —OCH₂—;

n is 1 or 2;

m is 1 or 2; and o is 0 or 1;

and pharmaceutically acceptable acid addition salts thereof.

Furthermore, the invention includes all racemic mixtures, all their corresponding enantiomers and/or optical isomers.

In one embodiment, compounds of the invention are those in which R³ is unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide.

In another embodiment, compounds of the present invention are compounds of formula I wherein X is a bond and $R^3$ is phenyl, which is unsubstituted or substituted by one to three substituents selected from the group consisting of lower alkyl, lower alkoxy, CN, $NO_2$, halogen, lower alkyl substituted by halogen, lower alkoxy substituted by halogen, aryl and sulfonamide, for example the following compound rac-[5-methanesulfonyl-2-((S)-2,2,2-trifluoro-1-methyl-ethoxy)-phenyl]-[3-(4-trifluoromethyl-phenyl)-pyrrolidin-1-yl]-methanone.

In yet another embodiment, compounds of the present invention are those wherein X is a —$CH_2$— and $R^3$ is phenyl, which is unsubstituted or substituted by one to three substituents selected from the group consisting of lower alkyl, lower alkoxy, CN, $NO_2$, halogen, lower alkyl substituted by halogen, lower alkoxy substituted by halogen, aryl and sulfonamide, for example the following compounds rac-[5-methanesulfonyl-2-((S)-2,2,2-trifluoro-1-methyl-ethoxy)-phenyl]-[3-(4-trifluoromethyl-benzyl)-pyrrolidin-1-yl]-methanone, rac-[5-methanesulfonyl-2-(2,2,3,3,3-pentafluoro-propoxy)-phenyl]-[3-(4-trifluoromethyl-benzyl)-pyrrolidin-1-yl]-methanone, rac-(4'-fluoro-4-methanesulfonyl-biphenyl-2-yl)-[3-(4-trifluoromethyl-benzyl)-pyrrolidin-1-yl]-methanone, rac-(2-cyclobutylmethoxy-5-methanesulfonyl-phenyl)-[3-(4-trifluoromethyl-benzyl)-pyrrolidin-1-yl]-methanone and rac-(2-cyclopentyloxy-5-methanesulfonyl-phenyl)-[3-(4-trifluoromethyl-benzyl)-pyrrolidin-1-yl]-methanone.

In a further embodiment, compounds of the present invention are those, wherein X is —$OCH_2$— and $R^3$ is phenyl, which is unsubstituted or substituted by one to three substituents selected from the group consisting of lower alkyl, lower alkoxy, CN, $NO_2$, halogen, lower alkyl substituted by halogen, lower alkoxy substituted by halogen, aryl and sulfonamide, for example the following compounds rac-[3-(4-chloro-phenoxymethyl)-pyrrolidin-1-yl]-[5-methanesulfonyl-2-((S)-2,2,2-trifluoro-1-methyl-ethoxy)-phenyl]-methanone, rac-[5-methanesulfonyl-2-((S)-2,2,2-trifluoro-1-methyl-ethoxy)-phenyl]-(3-p-tolyloxymethyl-pyrrolidin-1-yl)-methanone, rac-[3-(biphenyl-4-yloxymethyl)-pyrrolidin-1-yl]-[5-methanesulfonyl-2-((S)-2,2,2-trifluoro-1-methyl-ethoxy)-phenyl]-methanone, rac-4-{1-[5-methanesulfonyl-2-((S)-2,2,2-trifluoro-1-methyl-ethoxy)-benzoyl]-pyrrolidin-3-ylmethoxy}-benzonitrile, rac-[5-methanesulfonyl-2-((S)-2,2,2-trifluoro-1-methyl-ethoxy)-phenyl]-[3-(4-nitro-phenoxymethyl)-pyrrolidin-1-yl]-methanone, rac-[5-methanesulfonyl-2-((S)-2,2,2-trifluoro-1-methyl-ethoxy)-phenyl]-[3-(4-trifluoromethoxy-phenoxymethyl)-pyrrolidin-1-yl]-methanone, rac-[3-(3,4-dichloro-phenoxymethyl)-pyrrolidin-1-yl]-[5-methanesulfonyl-2-((S)-2,2,2-trifluoro-1-methyl-ethoxy)-phenyl]-methanone and rac-[5-methanesulfonyl-2-((S)-2,2,2-trifluoro-1-methyl-ethoxy)-phenyl]-[3-(3-methoxy-phenoxymethyl)-pyrrolidin-1-yl]-methanone.

In one embodiment, compounds of the invention are those wherein X is —NH—.

In another embodiment, compounds of the invention are those wherein X is —$CH_2O$—.

In yet another embodiment, compounds of the invention are those wherein X is —$CH_2$—.

In a further embodiment, compounds of the invention are those wherein X is —$OCH_2$—;

In another embodiment, compounds of the invention are those wherein X is a bond.

In one embodiment, compounds of the present invention are those wherein $R^3$ is unsubstituted phenyl.

In another embodiment, compounds of the invention are those wherein $R^3$ is phenyl substituted by halogen.

In yet another embodiment, compounds of the invention are those wherein $R^3$ is phenyl substituted by $CF_3$.

In a further embodiment, compounds of the invention are those wherein $R^3$ is phenyl substituted by lower alkoxy or lower alkoxy substituted by halogen.

In one embodiment, the compounds of the present invention are those in which $R^1$ is $OR^{1'}$. In particular, those compounds wherein $R^{1'}$ is lower alkyl or compounds in which $R^{1'}$ is lower alkyl substituted by halogen.

In another embodiment, the compounds of the present invention are those in which $R^1$ is heterocycloalkyl.

In a further embodiment, the compounds of the present invention are those in which $R^1$ is heteroaryl.

In one embodiment, the compounds of formula I are those wherein m is 1, especially those where n is 2.

In another embodiment, the compounds of formula I are those wherein n is 1, especially those where m is 2.

The present compounds of formula I and their pharmaceutically acceptable salts can be prepared by methods known in the art, for example, by processes (a)-(c) described below, which process comprises a) reacting a compound of formula

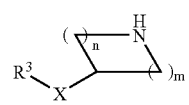

II with a compound of formula

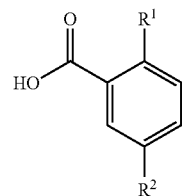

III in the presence of an activating agent, such as TBTU (2-(1H-benzotriazole-1-yl)-1,1,3,3-tetramethyluroniumtetrafluoroborate), to obtain a compound of formula

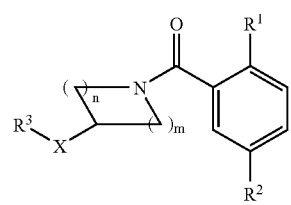

I wherein the substituents $R^1$, $R^2$ and $R^3$ are as defined above, and m and n are each independently 1 or 2;

b) reacting a compound of formula

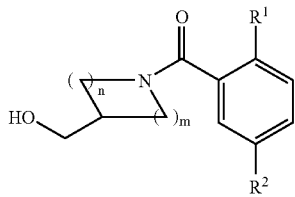

IV with a compound of formula $R^3$—OH under Mitsunobu conditions in the present of a phosphine to obtain a compound of formula

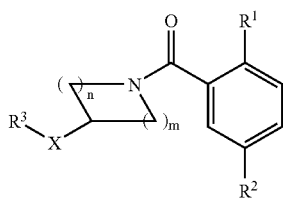

I wherein the substituents $R^1$, $R^2$ and $R^3$ are as defined above, X is —$OCH_2$— and m and n are each independently 1 or 2;

c) reacting a compound of formula

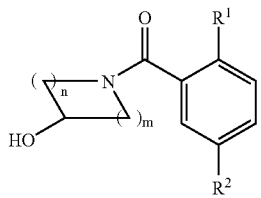

V with a compound of formula $R^3$—$CH_2$-Hal wherein Hal is an halogen atom like chlorine, bromine, or iodine in the presence of a base, such as sodium tert-butoxide, to a compound of formula

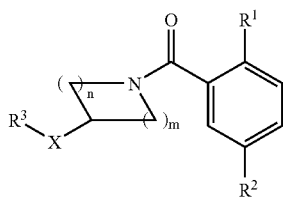

I wherein the substituents $R^1$, $R^2$ and $R^3$ are as defined above, X is —$CH_2O$— and m and n are each independently 1 or 2; and if desired, converting the compounds obtained into pharmaceutically acceptable acid addition salts.

The compounds of formula I can be prepared in accordance with process variants (a)-(c) and with the following schemes 1-3. The starting materials are either commercially available, are otherwise known in the chemical literature, or can be prepared in accordance with methods well known in the art.

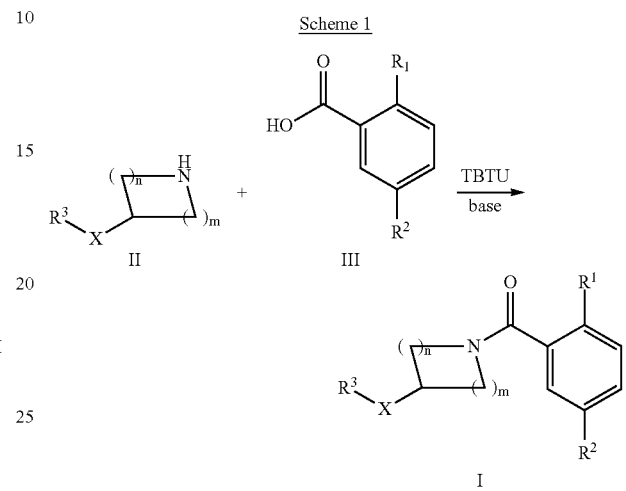

Compounds of general formula I can be prepared by reacting amine derivatives of formula II with an appropriately substituted acid of formula III in the presence of an activating agent, like TBTU (2-(1H-benzotriazole-1-yl)-1,1,3,3-tetramethyluroniumtetrafluoroborate), and a base, such as N-ethyldiisopropylamine (Scheme 1).

The amine compounds of formula II are either commercially available, are otherwise known in the chemical literature, or can be prepared using a variety of methods well known in the art.

The acids of formula III are either known in the chemical literature, or can be prepared using a variety of methods well known in the art.

Scheme 2

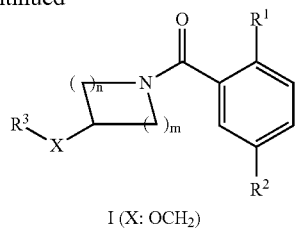

I (X: OCH$_2$)

Compounds of general formula I can also be prepared by alternative routes as shown in Scheme 2. For instance, compounds of formula I (X: OCH$_2$) can be prepared by reacting a hydroxy compound of formula IV with an alcohol of formula R$^3$—OH, under Mitsunobu reaction conditions in the presence of a phosphine like triphenylphosphine or diphenyl-2-pyridylphosphine and a dialkylazadicarboxylate, like di-tert-butyl azodicarboxylate or diethylazadicarboxylate. The compounds of formula IV can be prepared by reacting amines of formula VIII with an appropriately substituted acid of formula III in the presence of an activating agent like TBTU (2-(1H-benzotriazole-1-yl)-1,1,3,3-tetramethyluroniumtetrafluoroborate) and a base, such as N-ethyldiisopropylamine.

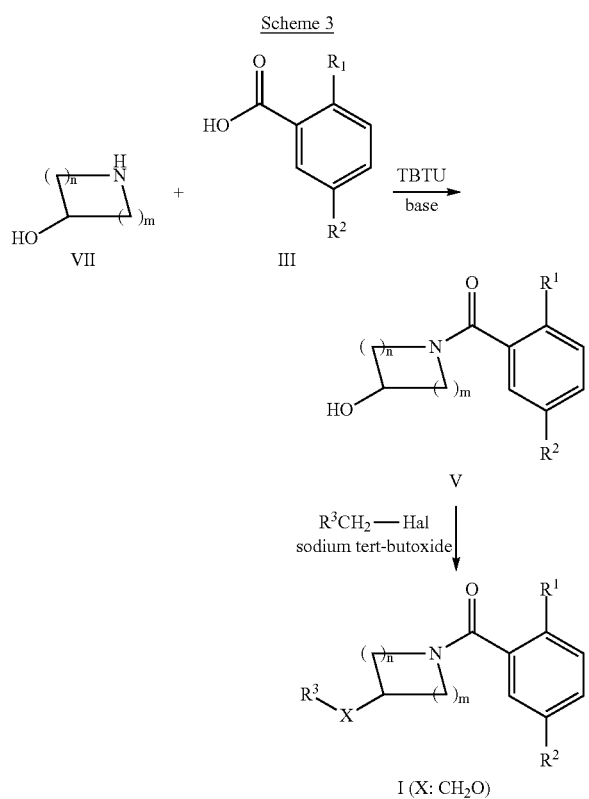

Compounds of general formula I can also be prepared by alternative routes as shown in Scheme 3. For instance, compounds of formula I (X: CH$_2$O) can be prepared by reacting a hydroxy compound of formula V with an alkylating agent of formula R$^3$—CH$_2$-Hal wherein Hal is an halogen atom like chlorine, bromine, or iodine in the presence of a base like sodium tert-butoxide. The compounds of formula V can be prepared by reacting amines of formula VIII with an appropriately substituted acid of formula III in the presence of an activating agent like TBTU (2-(1H-benzotriazole-1-yl)-1,1,3,3-tetramethyluroniumtetrafluoroborate) and a base, such as N-ethyldiisopropylamine.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I may be basic, for example in cases where the residue R$^3$ contains a basic group such as an aliphatic or aromatic amine moiety. In such cases the compounds of formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin 1% (Gibco life technologies), Hygromycin 0.6 mg/ml (Gibco life technologies), Glutamine 1 mM Gibco life technologies) Uptake buffer (UB): 150 mM NaCl, 10 mM Hepes-Tris, pH 7.4, 1 mM CaCl$_2$, 2.5 mM KCl, 2.5 mM MgSO$_4$, 10 mM (+) D-glucose. Flp-in™-CHO (Invitrogen Cat n° R758-07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 µM non-radioactive glycine. The plates were incubated with gentle shaking, and the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an $IC_{50}$ (µM) at GlyT-1 in the range of 0.09-0.50, as shown in the table below.

| Example No. | $IC_{50}$ (µM) |
| --- | --- |
| 2 | 0.22 |
| 11 | 0.11 |
| 13 | 0.09 |
| 14 | 0.50 |
| 15 | 0.24 |
| 16 | 0.32 |
| 29 | 0.20 |
| 30 | 0.27 |
| 31 | 0.45 |
| 32 | 0.21 |
| 33 | 0.17 |
| 35 | 0.13 |
| 36 | 0.13 |
| 37 | 0.17 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

Compounds of the invention are good inhibitors of the glycine transporter 1 (GlyT-1), and have good selectivity to glycine transporter 2 (GlyT-2) inhibitors. The invention further provides methods of treating diseases related to activation of NMDA receptors via Glyt-1 inhibition, in particular the treatment of such illnesses as psychoses, dysfunction in memory and learning, schizophrenia, dementia and other diseases in which cognitive processes are impaired, such as attention deficit disorders or Alzheimer's disease.

The most preferred indications in accordance with the present invention are those, which include disorders of the central nervous system, for example the treatment or prevention of schizophrenia, cognitive impairment and Alzheimer's disease. The invention provides a method for treating schizophrenia which comprises administering to an individual a therapeutically effective amount of a compound of formula I or a pharmaceutically acceptable salt thereof. The invention provides a method for treating cognitive impairment which comprises administering to an individual a therapeutically effective amount of a compound of formula I or a pharmaceutically acceptable salt thereof. The invention provides a method for treating Alzheimer's disease which comprises administering to an individual a therapeutically effective amount of a compound of formula I or a pharmaceutically acceptable salt thereof.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

Tablet Formulation (Wet Granulation)

| | | mg/tablet | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  |  | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
|  | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following examples illustrate the invention but are not intended to limit its scope. The following abbreviations were used in the examples:

TBTU: 2-(1H-benzotriazole-1-yl)-1,1,3,3-tetramethyluroniumtetrafluoroborate;

Synthesis of Intermediates of Formula II

EXAMPLE A1

Rac-3-(4-Trifluoromethyl-phenyl)-pyrrolidine a) rac-3-Hydroxy-3-(4-trifluoromethyl-phenyl)-pyrrolidine-1-carboxylic acid ethyl ester

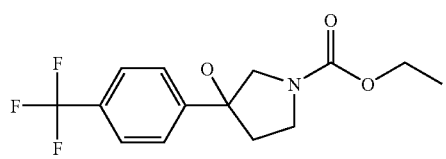

364 mg magnesium was suspended in 2 ml ether, under nitrogen. 150 ul 4-bromobenzo-trifluoride was added and then a solution of 12.6 mmol 4-bromobenzotrifluoride in 1.5 ml ether was added dropwise over a period of 10 minutes at room temperature. The mixture came mildly exothermic and turned red-brown while the grignard reagent formed during 1.5 h of stirring. The mixture was cooled down to 0° C. A solution of 12.5 mmol 1-N-ethoxycarbonyl-3-pyrrolidone in 14 ml ether was added dropwise. The reaction mixture was allowed to come to room temperature and stirred for 2 h30. 20% NH$_4$Cl was added dropwise, at 0° C., to quench the reaction. The mixture was allowed to warm to room temperature. The aqueous layer was extracted 3 times with ether. The combined organic phases were washed with water and brine, dried over Na$_2$SO$_4$ and evaporated. The residue was purified on silica gel (eluent: heptane-ethyl acetate 1/1) to yield the title compound (61%) as a yellow solid. MS (m/e): 362.2 ([M+59], 100%).

b) rac-3-(4-Trifluoromethyl-phenyl)-pyrrolidin-3-ol

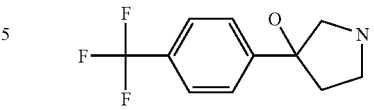

To a solution of 1.98 mmol rac-3-Hydroxy-3-(4-trifluoromethyl-phenyl)-pyrrolidine-1-carboxylic acid ethyl ester in 15 ml dioxane., was added 8 ml of a 2.5N solution of KOH in butanol. The solution was stirred under reflux for 2 hours. The solvent was removed in vacuo and the residue was taken in water. The aqueous phase was extracted 3 times with dichloromethane. The combined organic phases were dried over Na$_2$SO$_4$, evaporated and dried. The compound was suspended in hexane/ether (~2:1), filtered and rinsed with hexane to yield the title compound (57%) as a light brown solid MS (m/e): 232.1 ([M+1], 100%).

c) 3-(4-Trifluoromethyl-phenyl)-2,5-dihydro-1H-pyrrole

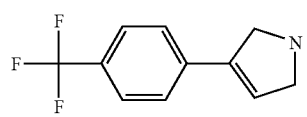

To a suspension of 0.43 mmol rac-3-(4-Trifluoromethyl-phenyl)-pyrrolidin-3-ol in 0.4 ml dichloromethane under argon, was added 0.4 ml TFA. The reaction mixture was stirred at reflux for 5 days and concentrated. The residue was dissolved in ethyl acetate and NaOH 2N was added until pH 9-10. The organic phases were dried over Na$_2$SO$_4$ and evaporated to yield the title compound (18%) as an oil MS (m/e): 214.2 ([M+1], 100%).

d) 3-(4-Trifluoromethyl-phenyl)-pyrrolidine

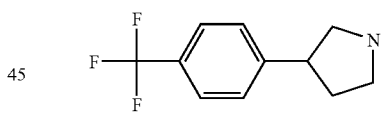

0.08 mmol 3-(4-Trifluoromethyl-phenyl)-2,5-dihydro-1H-pyrrole was dissolved in MeOH and HCl in ether was added until pH 1. After 5 minutes stirring, the solvents were evaporated. To a solution of this salt in 0.7 ml methanol under argon was added 2 mg Pd/C 10% and the mixture was hydrogenated under atmospheric pressure of hydrogen at room temperature for 4 h. The mixture was cooled, flushed with argon, diluted with methanol, filtered and the solvent was removed in vacuo to yield the title compound (64%) as an oil MS (m/e): 216.3 ([M+1], 100%).

EXAMPLE A2

Rac-3-o-Tolyl-pyrrolidine a) rac-3-Hydroxy-3-o-tolyl-pyrrolidine-1-carboxylic acid tert-butyl ester

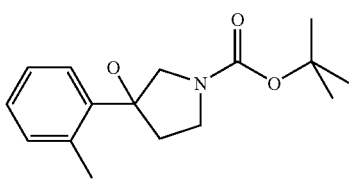

Prepared in analogy to Example A1 (a) from N-boc-3-pyrrolidinone and o-tolyl-magnesiumbromide to yield the title compound as an light yellow oil. MS (m/e): 278.2 (M+H⁺, 100%).

b) 3-o-Tolyl-2,5-dihydro-1H-pyrrole

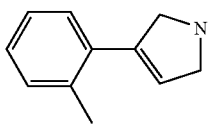

Prepared in analogy to Example A1(c) from rac-3-Hydroxy-3-o-tolyl-pyrrolidine-1-carboxylic acid tert-butyl ester to yield the title compound as an orange oil. MS (m/e): 160.2 (M+H⁺, 100%).

c) Rac-3-o-Tolyl-pyrrolidine

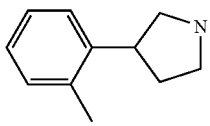

Prepared in analogy to Example B3 from 3-o-Tolyl-2,5-dihydro-1H-pyrrole to yield the title compound as a yellow oil. MS (m/e): 162.3 (M+H⁺, 100%).

EXAMPLE A3

Rac-3-(4-Trifluoromethyl-benzyl)-pyrrolidine acetic acid

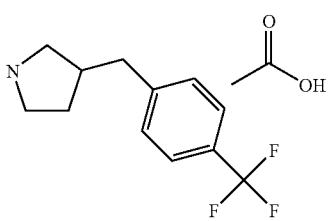

Prepared in analogy to Example A1(d) from 1-Benzyl-3-(4-trifluoromethyl-benzyl)-pyrrolidine (CAS: 336182-64-0) by replacing HCl with acetic acid to yield the title compound as an light brown oil. MS (m/e): 230.4 (M+H⁺, 100%).

EXAMPLE A4

Rac-3-(3-Fluoro-benzyl)-pyrrolidine

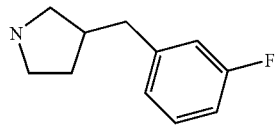

Prepared in analogy to Example A1 (d) from 1-Benzyl-3-(3-fluoro-benzyl)-pyrrolidine to yield the title compound as a colorless oil. MS (m/e): 180 (M+H⁺, 100%).

EXAMPLE A5

Rac-pyrrolidin-3-yl-(4-trifluoromethyl-phenyl)-amine hydrochloride

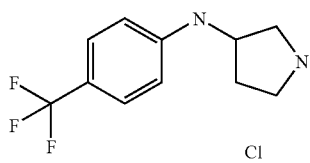

Prepared in analogy to Example A1(d) from (1-Benzyl-pyrrolidin-3-yl)-(4-trifluoromethyl-phenyl)-amine (CAS: 816468-46-9) to yield the title compound as a white solid. MS (m/e): 230.9 (M+H⁺, 100%).

EXAMPLE B1

4'-Fluoro-4-methanesulfonyl-biphenyl-2-carboxylic acid

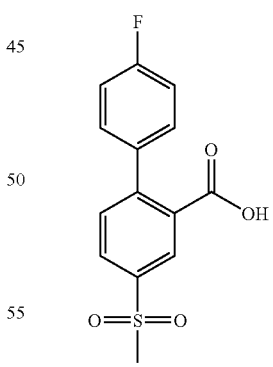

A mixture of 6.1 mmol 2-Iodo-5-methanesulfonyl-benzoic acid (CAS: 845616-08-2), 12.2 mmol 4-fluorobenzeneboronic acid, 18.4 mmol sodium carbonate and 0.3 mmol palladium (II) acetate in 30 ml water was stirred at room temperature for 48 hours. The mixture was filtered and the filtrate was acidified with HCl 37%. The mixture was stirred at room temperature for 30 minutes. The solid was filtered, washed with water and dried to provide the title compound (92%). Yellow solid. MS (m/e): 293.2 ([M−H], 100%).

EXAMPLE B2

5-Methanesulfonyl-2-(4-methyl-pyrazol-1-yl)-benzoic acid a) 5-Methanesulfonyl-2-(4-methyl-pyrazol-1-yl)-benzoic acid methyl ester

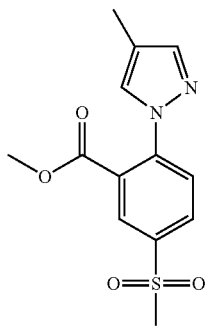

In a glass tube was added successively 0.29 mmol 2-Iodo-5-methanesulfonyl-benzoic acid methyl ester (CAS: 847547-09-5), 0.35 mmol 4-methylpyrazole, 0.59 mmol potassium carbonate, 0.06 mmol CuI and a solution of 0.12 mmol trans-1,2-diaminocyclohexane in 0.4 ml dioxane (degased). The tube was filled with argon and sealed with a cap. The reaction mixture was heated at 120° C. overnight. The reaction mixture was cooled down to room temperature, dichloromethane and water were added. The aqueous phase was extracted 2 times with dichloromethane. The combined organic phases were dried over sodium sulfate and evaporated. The crude compound was purified on a 10 g Flashpack cartridge. Eluent: Heptane/ethylacetate to provide the title compound (57%) as a light yellow oil. MS (m/e): 295.0([M+H]$^+$, 100%).

(b) 5-Methanesulfonyl-2-(4-methyl-pyrazol-1-yl)-benzoic acid

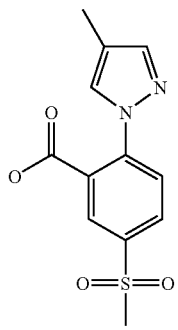

To 2.08 mmol 5-Methanesulfonyl-2-(4-methyl-pyrazol-1-yl)-benzoic acid methyl ester in 2.2 ml THF and 2.2 ml water was added 3.12 mmol lithium hydroxide and the reaction mixture was stirred at RT for 2 hours. After such time the solvent was removed in vacuo, the residue was taken in water and acidified by addition of 3N HCl to yield after filtration the title compound as a white solid (88%). MS (m/e): 279.1 ([M−H], 100%).

EXAMPLE B3

5-Methanesulfonyl-2-(tetrahydro-pyran-4-yl)-benzoic acid

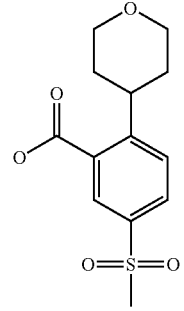

To 0.07 mmol 2-(3,6-Dihydro-2H-pyran-4-yl)-5-methanesulfonyl-benzoic acid (CAS: 847547-05-1) in 0.5 ml methanol under argon was added 20 mg Pd/C, followed by 0.07 mmol ammonium formate. The reaction mixture was refluxed for 30 minutes, filtered and evaporated. Water was added and the solution was acidified with 2N HCl to pH 1. The aqueous phase was extracted with dichloromethane. The combined organic phases were dried over Na$_2$SO$_4$ and evaporated to yield the title compound as a colorless oil. MS (m/e): 283.2 ([M−H], 100%).

EXAMPLE C1

Rac-(3-Hydroxymethyl-pyrrolidin-1-yl)-[5-methanesulfonyl-2-((S)-2,2,2-trifluoro-1-methyl-ethoxy)-phenyl]-methanone

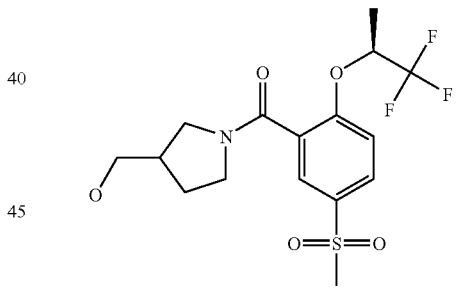

To a solution of 0.01 mol 5-Methanesulfonyl-2-((S)-2,2,2-trifluoro-1-methyl-ethoxy)-benzoic acid (CAS: 845616-82-2) in 40 ml N,N-dimethylformamide were added successively 3.57 g TBTU, 8.5 ml N-ethyldiisopropylamine and 1 g rac-pyrrolidin-3-yl-methanol (CAS: 5082-74-6). The reaction mixture was stirred at room temperature for 16 h and then concentrated in vacuo. The mixture was taken in ethyl acetate and washed twice with water and twice with saturated NaHCO$_3$. The organic phase was dried over Na$_2$SO$_4$ and filtered. The solvent was evaporated. The crude oil was purified on silica gel (eluent: ethyl acetate) to yield the title compound as an off white foam. MS (m/e): 396.1 (M+H$^+$, 100%).

Synthesis of Compounds of Formula I

In analogy to Example C1, compounds 1 to 27 of the following table were prepared from the acid derivatives and amine derivatives:

| Expl. No. | Structure | Systematic Name MW found [M + H⁺] | Starting materials | MW |
|---|---|---|---|---|
| 1 | 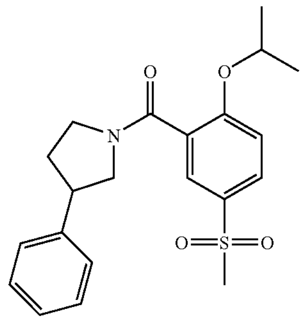 | rac-(2-Isopropoxy-5-methanesulfonyl-phenyl)-(3-phenyl-pyrrolidin-1-yl)-methanone 388.3 | rac-3-Phenyl-pyrrolidine (CAS: 936-44-7) and 2-Isopropoxy-5-methanesulfonyl-benzoic acid (CAS: 845616-02-6) | 387.4 |
| 2 | 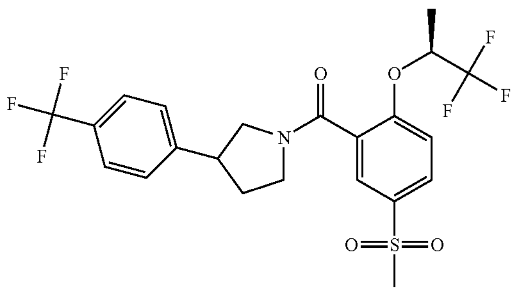 | rac-[5-Methanesulfonyl-2-((S)-2,2,2-trifluoro-1-methyl-ethoxy)-phenyl]-[3-(4-trifluoromethyl-phenyl)-pyrrolidin-1-yl]-methanone 510.2 | rac-3-(4-Trifluoromethyl-phenyl)-pyrrolidine (Example A1) and 5-Methanesulfonyl-2-((S)-2,2,2-trifluoro-1-methyl-ethoxy)-benzoic acid (CAS: 845616-82-2) | 509.4 |
| 3 | 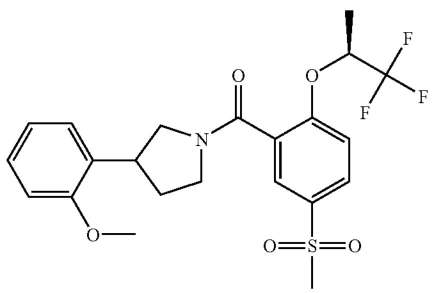 | rac-[5-Methanesulfonyl-2-((S)-2,2,2-trifluoro-1-methyl-ethoxy)-phenyl]-[3-(2-methoxy-phenyl)-pyrrolidin-1-yl]-methanone 472.2 | rac-3-(2-Methoxy-phenyl)-pyrrolidine (CAS: 91246-24-1) and 5-Methanesulfonyl-2-((S)-2,2,2-trifluoro-1-methyl-ethoxy)-benzoic acid (CAS: 845616-82-2) | 471.4 |
| 4 | 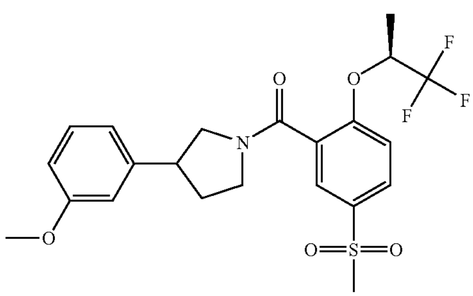 | rac-[5-Methanesulfonyl-2-((S)-2,2,2-trifluoro-1-methyl-ethoxy)-phenyl]-[3-(3-methoxy-phenyl)-pyrrolidin-1-yl]-methanone 472.2 | rac-3-(3-Methoxy-phenyl)-pyrrolidine (CAS: 38175-35-8) and 5-Methanesulfonyl-2-((S)-2,2,2-trifluoro-1-methyl-ethoxy)-benzoic acid (CAS: 845616-82-2) | 471.4 |
| 5 | 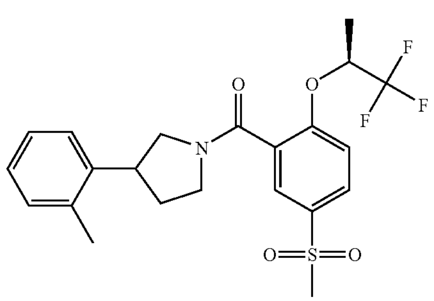 | rac-[5-Methanesulfonyl-2-((S)-2,2,2-trifluoro-1-methyl-ethoxy)-phenyl]-(3-o-tolyl-pyrrolidin-1-yl)-methanone 456.4 | rac-rac-3-o-Tolyl-pyrrolidine (Example A2) and 5-Methanesulfonyl-2-((S)-2,2,2-trifluoro-1-methyl-ethoxy)-benzoic acid (CAS: 845616-82-2) | 455.4 |

-continued

| Expl. No. | Structure | Systematic Name MW found [M + H⁺] | Starting materials | MW |
|---|---|---|---|---|
| 6 | 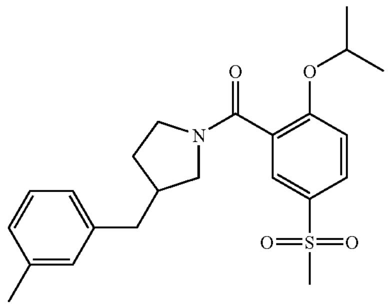 | rac-(2-Isopropoxy-5-methanesulfonyl-phenyl)-[3-(3-methyl-benzyl)-pyrrolidin-1-yl]-methanone 416 | rac-3-(3-Methyl-benzyl)-pyrrolidine (CAS: 887594-96-9) and 2-Isopropoxy-5-methanesulfonyl-benzoic acid (CAS: 845616-02-6) | 415.5 |
| 7 | 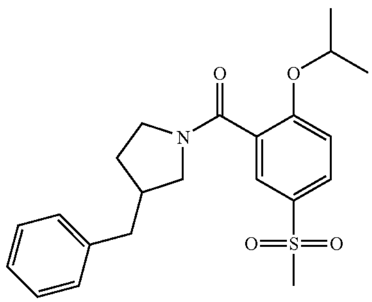 | rac-(3-Benzyl-pyrrolidin-1-yl)-(2-isopropoxy-5-methanesulfonyl-phenyl)-methanone 402.3 | rac-3-Benzyl-pyrrolidine (CAS: 170304-83-3) and 2-Isopropoxy-5-methanesulfonyl-benzoic acid (CAS: 845616-02-6) | 401.5 |
| 8 | 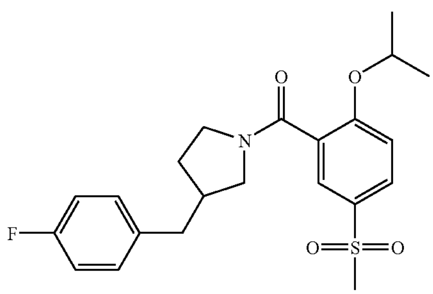 | rac-[3-(4-Fluoro-benzyl)-pyrrolidin-1-yl]-(2-isopropoxy-5-methanesulfonyl-phenyl)-methanone 420.2 | rac-3-(4-Fluoro-benzyl)-pyrrolidine (CAS: 193220-17-6) and 2-Isopropoxy-5-methanesulfonyl-benzoic acid (CAS: 845616-02-6) | 419.5 |
| 9 | 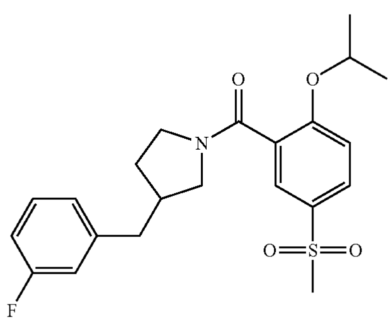 | rac-[3-(3-Fluoro-benzyl)-pyrrolidin-1-yl]-(2-isopropoxy-5-methanesulfonyl-phenyl)-methanone 420.2 | rac-3-(3-Fluoro-benzyl)-pyrrolidine (Example A4) and 2-Isopropoxy-5-methanesulfonyl-benzoic acid (CAS: 845616-02-6) | 419.5 |
| 10 | 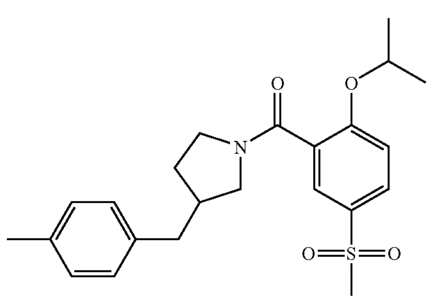 | rac-(2-Isopropoxy-5-methanesulfonyl-phenyl)-[3-(4-methyl-benzyl)-pyrrolidin-1-yl]-methanone 416.3 | rac-3-(4-Methyl-benzyl)-pyrrolidine (CAS: 193220-16-5) and 2-Isopropoxy-5-methanesulfonyl-benzoic acid (CAS: 845616-02-6) | 415.5 |

-continued

| Expl. No. | Structure | Systematic Name MW found [M + H⁺] | Starting materials | MW |
|---|---|---|---|---|
| 11 | 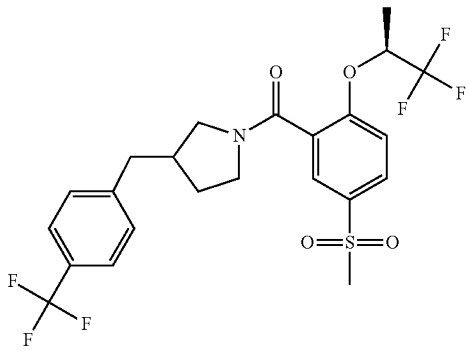 | rac-[5-Methanesulfonyl-2-((S)-2,2,2-trifluoro-1-methyl-ethoxy)-phenyl]-[3-(4-trifluoromethyl-benzyl)-pyrrolidin-1-yl]-methanone 524.3 | rac-3-(4-Trifluoromethyl-benzyl)-pyrrolidine acetic acid (Example A3) and 5-Methanesulfonyl-2-((S)-2,2,2-trifluoro-1-methyl-ethoxy)-benzoic acid (CAS: 845616-82-2) | 523.4 |
| 12 | 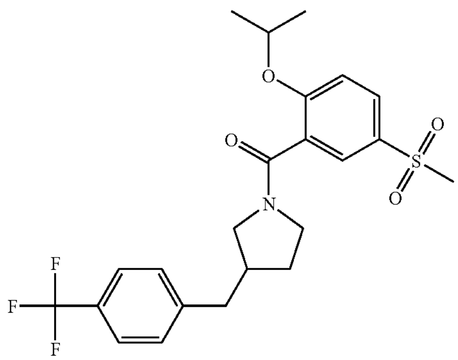 | rac-(2-Isopropoxy-5-methanesulfonyl-phenyl)-[3-(4-trifluoromethyl-benzyl)-pyrrolidin-1-yl]-methanone 470.2 | rac-3-(4-Trifluoromethyl-benzyl)-pyrrolidine acetic acid (Example A3) and 2-Isopropoxy-5-methanesulfonyl-benzoic acid (CAS: 845616-02-6) | 469.5 |
| 13 | 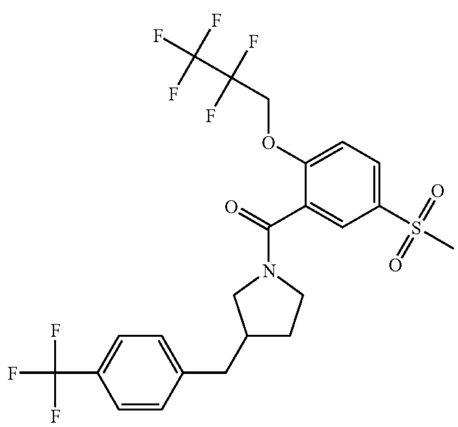 | rac-[5-Methanesulfonyl-2-(2,2,3,3,3-pentafluoro-propoxy)-phenyl]-[3-(4-trifluoromethyl-benzyl)-pyrrolidin-1-yl]-methanone 560.2 | rac-3-(4-Trifluoromethyl-benzyl)-pyrrolidine acetic acid (Example A3) and 5-Methanesulfonyl-2-(2,2,3,3,3-pentafluoro-propoxy)-benzoic acid (CAS: 845616-42-4) | 559.4 |
| 14 | 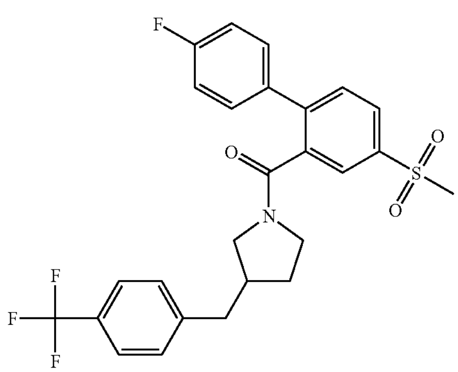 | rac-(4'-Fluoro-4-methanesulfonyl-biphenyl-2-yl)-[3-(4-trifluoromethyl-benzyl)-pyrrolidin-1-yl]-methanone 506.2 | rac-3-(4-Trifluoromethyl-benzyl)-pyrrolidine acetic acid (Example A3) and 4'-Fluoro-4-methanesulfonyl-biphenyl-2-carboxylic acid (example B1) | 505.5 |

| Expl. No. | Structure | Systematic Name MW found [M + H⁺] | Starting materials | MW |
|---|---|---|---|---|
| 15 | 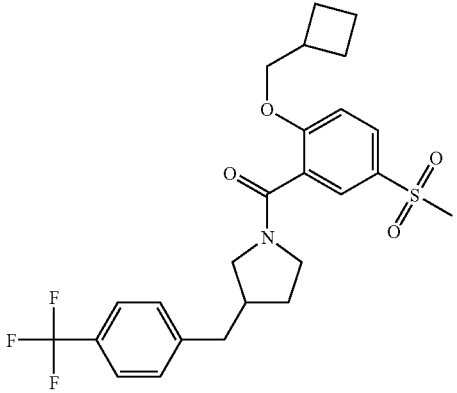 | rac-(2-Cyclobutylmethoxy-5-methanesulfonyl-phenyl)-[3-(4-trifluoromethyl-benzyl)-pyrrolidin-1-yl]-methanone 496.3 | rac-3-(4-Trifluoromethyl-benzyl)-pyrrolidine acetic acid (Example A3) and 2-Cyclobutylmethoxy-5-methanesulfonyl-benzoic acid (CAS: 845616-33-3) | 495.5 |
| 16 | 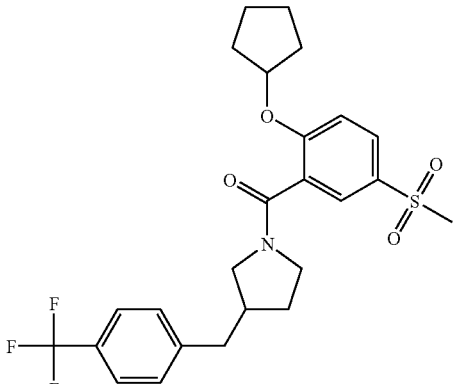 | rac-(2-Cyclopentyloxy-5-methanesulfonyl-phenyl)-[3-(4-trifluoromethyl-benzyl)-pyrrolidin-1-yl]-methanone 496.3 | rac-3-(4-Trifluoromethyl-benzyl)-pyrrolidine acetic acid (Example A3) and 2-Cyclopentyloxy-5-methanesulfonyl-benzoic acid (CAS: 845616-05-9) | 495.5 |
| 17 | 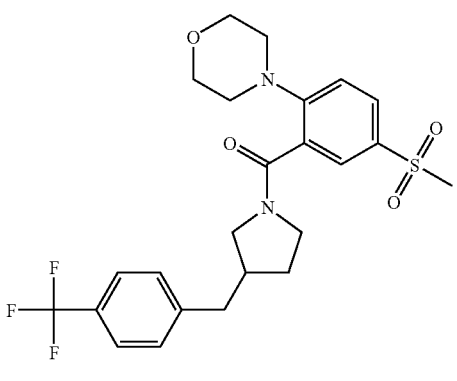 | rac-(5-Methanesulfonyl-2-morpholin-4-yl-phenyl)-[3-(4-trifluoromethyl-benzyl)-pyrrolidin-1-yl]-methanone 497.3 | rac-3-(4-Trifluoromethyl-benzyl)-pyrrolidine acetic acid (Example A3) and 5-Methanesulfonyl-2-morpholin-4-yl-benzoic acid (CAS: 847971-96-4) | 496.5 |
| 18 | 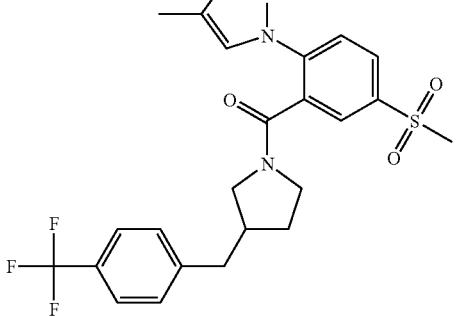 | rac-[5-Methanesulfonyl-2-(4-methyl-pyrazol-1-yl)-phenyl]-[3-(4-trifluoromethyl-benzyl)-pyrrolidin-1-yl]-methanone 492.2 | rac-3-(4-Trifluoromethyl-benzyl)-pyrrolidine acetic acid (Example A3) and 5-Methanesulfonyl-2-(4-methyl-pyrazol-1-yl)-benzoic acid (example B2) | 491.5 |

| Expl. No. | Structure | Systematic Name MW found [M + H⁺] | Starting materials | MW |
|---|---|---|---|---|
| 19 | 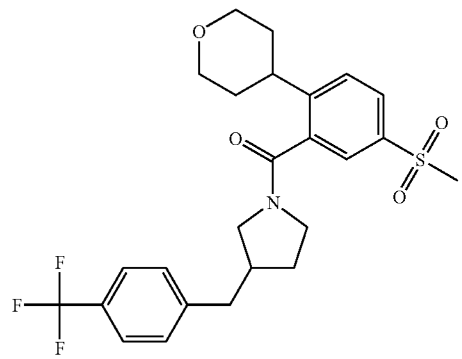 | rac-[5-Methanesulfonyl-2-(tetrahydro-pyran-4-yl)-phenyl]-[3-(4-trifluoromethyl-benzyl)-pyrrolidin-1-yl]-methanone 496.3 | rac-3-(4-Trifluoromethyl-benzyl)-pyrrolidine acetic acid (Example A3) and 5-Methanesulfonyl-2-(tetrahydro-pyran-4-yl)-benzoic acid (example B3) | 495.5 |
| 20 | 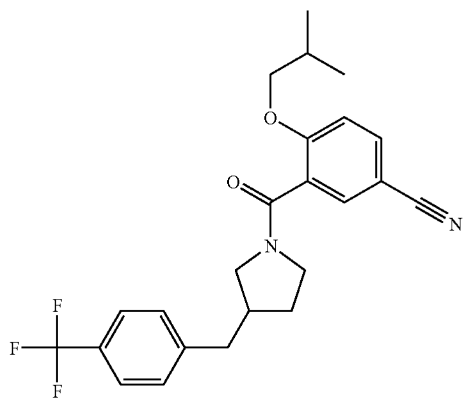 | rac-4-Isobutoxy-3-[3-(4-trifluoromethyl-benzyl)-pyrrolidine-1-carbonyl]-benzonitrile 431.3 | rac-3-(4-Trifluoromethyl-benzyl)-pyrrolidine acetic acid (Example A3) and 5-Cyano-2-isobutoxy-benzoic acid (CAS: 845616-16-2) | 430.4 |
| 21 | 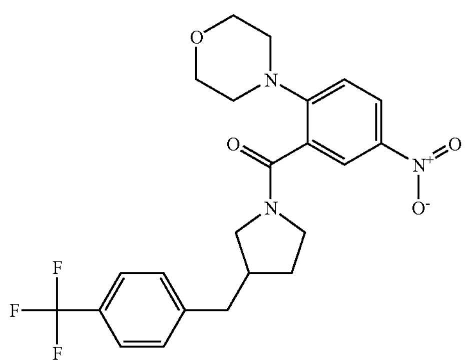 | rac-(2-Morpholin-4-yl-5-nitro-phenyl)-[3-(4-trifluoromethyl-benzyl)-pyrrolidin-1-yl]-methanone 464.3 | rac-3-(4-Trifluoromethyl-benzyl)-pyrrolidine acetic acid (Example A3) and 2-Morpholin-4-yl-5-nitro-benzoic acid (CAS: 4036-83-3) | 463.4 |
| 22 | 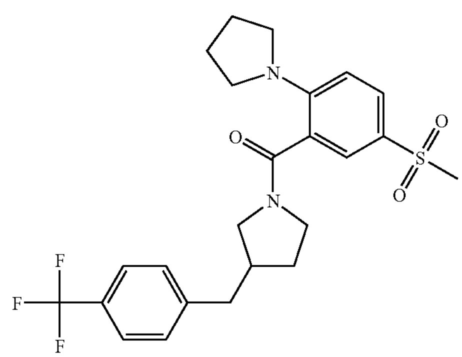 | rac-(5-Methanesulfonyl-2-pyrrolidin-1-yl-phenyl)-[3-(4-trifluoromethyl-benzyl)-pyrrolidin-1-yl]-methanone 481.3 | rac-3-(4-Trifluoromethyl-benzyl)-pyrrolidine acetic acid (Example A3) and 5-Methanesulfonyl-2-pyrrolidin-1-yl-benzoic acid (CAS: 847971-88-4) | 480.5 |

| Expl. No. | Structure | Systematic Name MW found [M + H⁺] | Starting materials | MW |
|---|---|---|---|---|
| 23 | 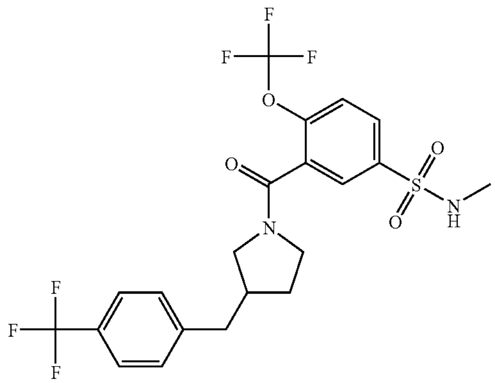 | rac-N-Methyl-4-trifluoromethoxy-3-[3-(4-trifluoromethyl-benzyl)-pyrrolidine-1-carbonyl]-benzenesulfonamide 511.3 | rac-3-(4-Trifluoromethyl-benzyl)-pyrrolidine acetic acid (Example A3) and 5-Methylsulfamoyl-2-trifluoromethoxy-benzoic acid (CAS: 845616-28-6) | 510.4 |
| 24 | 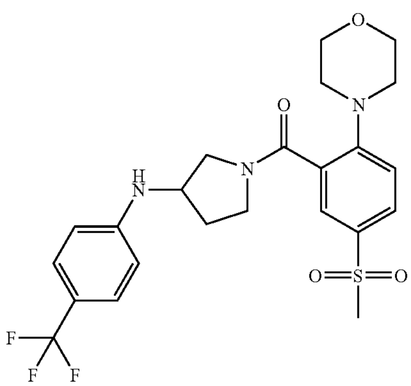 | rac-(5-Methanesulfonyl-2-morpholin-4-yl-phenyl)-[3-(4-trifluoromethyl-phenylamino)-pyrrolidin-1-yl]-methanone 498.0 | rac-Pyrrolidin-3-yl-(4-trifluoromethyl-phenyl)-amine hydrochloride (Example A5) and 5-Methanesulfonyl-2-morpholin-4-yl-benzoic acid (CAS: 847971-96-4) | 497.5 |
| 25 | 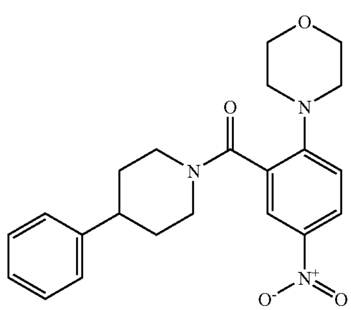 | (2-Morpholin-4-yl-5-nitro-phenyl)-(4-phenyl-piperidin-1-yl)-methanone 396.2 | 1-Methyl-4-phenyl-piperidine (commercial) and 2-Morpholin-4-yl-5-nitro-benzoic acid (CAS: 4036-83-3) | 395.4 |
| 26 | 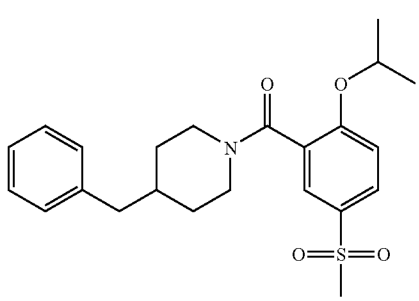 | (4-Benzyl-piperidin-1-yl)-(2-isopropoxy-5-methanesulfonyl-phenyl)-methanone 416.4 | 4-benzylpiperidine (commercial) and 2-Isopropoxy-5-methanesulfonyl-benzoic acid (CAS: 845616-02-6) | 415.5 |

| Expl. No. | Structure | Systematic Name MW found [M + H+] | Starting materials | MW |
|---|---|---|---|---|
| 27 | 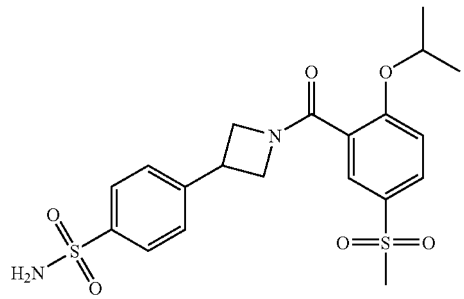 | 4-[1-(2-Isopropoxy-5-methanesulfonyl-benzoyl)-azetidin-3-yl]-benzenesulfonamide 511.2 (M + OAc) | 4-Azetidin-3-yl-benzenesulfonamide and 2-Isopropoxy-5-methanesulfonyl-benzoic acid (CAS: 845616-02-6) | 452.5 |

Example 28 rac-[5-Methanesulfonyl-2-((S)-2,2,2-trifluoro-1-methyl-ethoxy)-phenyl]-[3-(4-trifluoromethyl-phenoxymethyl)-pyrrolidin-1-yl]-methanone

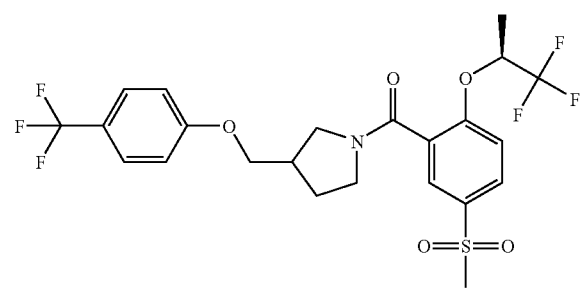

To a solution of 70 mg rac-(3-Hydroxymethyl-pyrrolidin-1-yl)-[5-methanesulfonyl-2-((S)-2,2,2-trifluoro-1-methyl-ethoxy)-phenyl]-methanone (Example C1) in 1.4 ml tetrahydrofuran were added 30 mg 4-hydroxybenzotrifluoride and 50 mg diphenyl-2-pyridylphosphine. 43 mg Di-tert-butyl azodicarboxylate was added. The mixture was stirred at 70° C. for 23 hours. The solvent was removed in vacuo. The oil was purified on silica gel (eluent: ethyl acetate) to yield a yellow gum. The gum was dissolved in ethyl acetate. The solution was washed 3 times with HCl 5N, once with water, dried over $Na_2SO_4$, filtered and concentrated in vacuo to provide the title compound as a light yellow foam. MS (m/e): 540.3 (M+H+, 100%).

In analogy to Example 28, compounds 29 to 39 of the following table were prepared from rac-(3-Hydroxymethyl-pyrrolidin-1-yl)-[5-methanesulfonyl-2-((S)-2,2,2-trifluoro-1-methyl-ethoxy)-phenyl]-methanone (Example C1) and the phenol reagent:

| Expl. No. | Structure | Systematic Name MW found [M + H+] | Starting materials | MW |
|---|---|---|---|---|
| 29 | 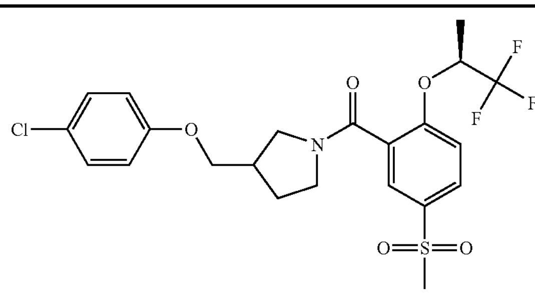 | rac-[3-(4-Chloro-phenoxymethyl)-pyrrolidin-1-yl]-[5-methanesulfonyl-2-((S)-2,2,2-trifluoro-1-methyl-ethoxy)-phenyl]-methanone 506.1 | 4-Chlorophenol and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 505.9 |
| 30 | 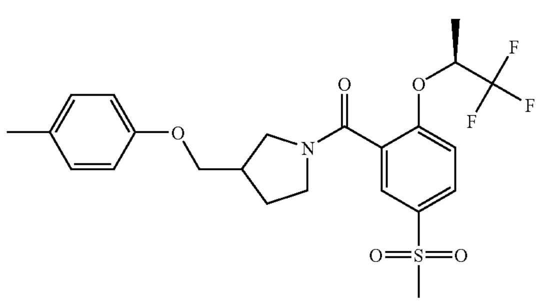 | rac-[5-Methanesulfonyl-2-((S)-2,2,2-trifluoro-1-methyl-ethoxy)-phenyl]-(3-p-tolyloxymethyl-pyrrolidin-1-yl)-methanone 486.2 | p-cresol and rac-(3-Hydroxymethyl-pyrrolidin-1-yl)-[5-methansulfonyl-2-((S)-2,2,2-trifluoro-1-methyl-ethoxy)-phenyl]-methanone (Example C1) | 485.5 |

| Expl. No. | Structure | Systematic Name MW found [M + H⁺] | Starting materials | MW |
|---|---|---|---|---|
| 31 | 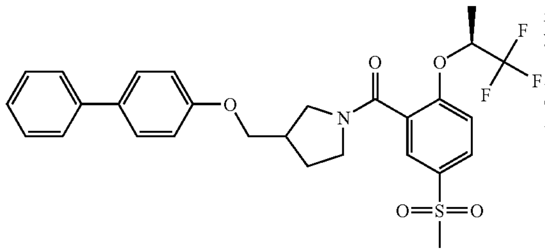 | rac-[3-(Biphenyl-4-yloxymethyl)-pyrrolidin-1-yl]-[5-methanesulfonyl-2-((S)-2,2,2-trifluoro-1-methyl-ethoxy)-phenyl]-methanone 548.3 | 4-hydroxybiphenyl and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 547.5 |
| 32 | 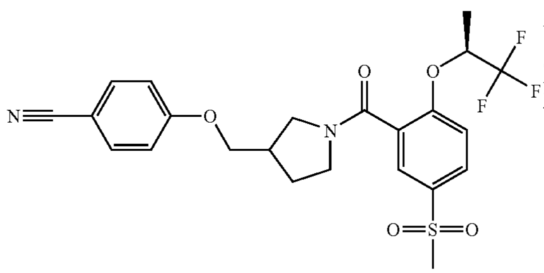 | rac-4-{1-[5-Methanesulfonyl-2-((S)-2,2,2-trifluoro-1-methyl-ethoxy)-benzoyl]-pyrrolidin-3-ylmethoxy}-benzonitrile 497.0 | 4-hydroxybenzonitrile and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 496.5 |
| 33 | 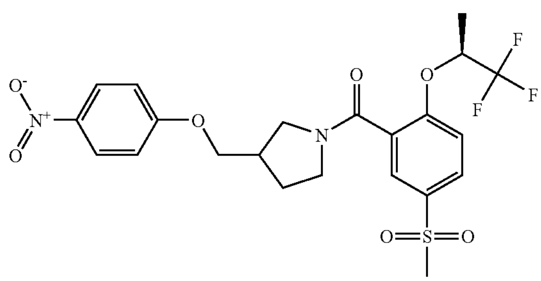 | rac-[5-Methanesulfonyl-2-((S)-2,2,2-trifluoro-1-methyl-ethoxy)-phenyl]-[3-(4-nitro-phenoxymethyl)-pyrrolidin-1-yl]-methanone 517.1 | 4-nitrophenol and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 516.4 |
| 34 | 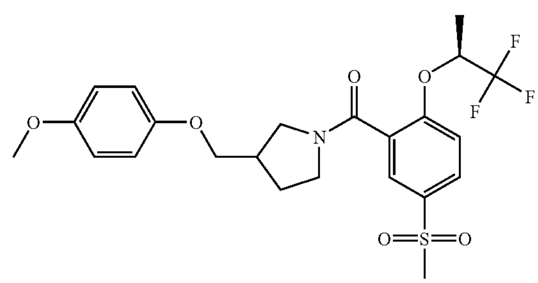 | rac-[5-Methanesulfonyl-2-((S)-2,2,2-trifluoro-1-methyl-ethoxy)-phenyl]-[3-(4-methoxy-phenoxymethyl)-pyrrolidin-1-yl]-methanone 502.0 | hydroquinone-monomethylether and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 501.5 |
| 35 | 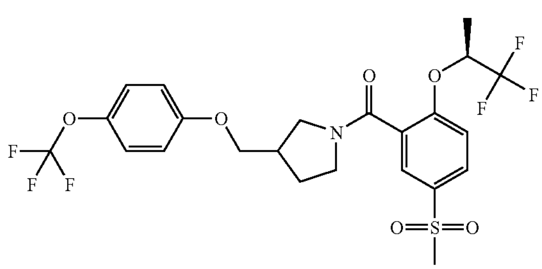 | rac-[5-Methanesulfonyl-2-((S)-2,2,2-trifluoro-1-methyl-ethoxy)-phenyl]-[3-(4-trifluoromethoxy-phenoxymethyl)-pyrrolidin-1-yl]-methanone 556.1 | 4-trifluoromethoxy-phenol and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 555.4 |

| Expl. No. | Structure | Systematic Name MW found [M + H+] | Starting materials | MW |
|---|---|---|---|---|
| 36 | 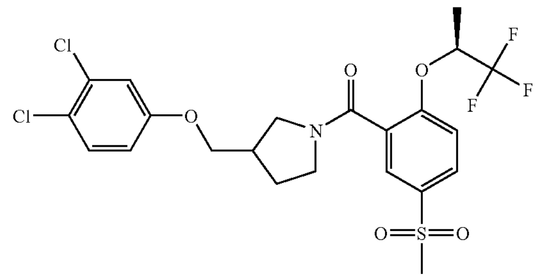 | rac-[3-(3,4-Dichloro-phenoxymethyl)-pyrrolidin-1-yl]-[5-methanesulfonyl-2-((S)-2,2,2-trifluoro-1-methyl-ethoxy)-phenyl]-methanone 540.2 | 3,4-dichlorophenol and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 540.3 |
| 37 | 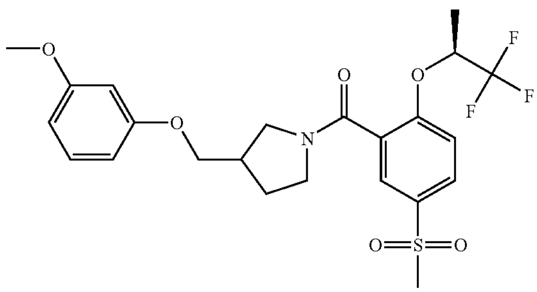 | rac-[5-Methanesulfonyl-2-((S)-2,2,2-trifluoro-1-methyl-ethoxy)-phenyl]-[3-(3-methoxy-phenoxymethyl)-pyrrolidin-1-yl]-methanone 502.0 | 3-methoxyphenol and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 501.5 |
| 38 | 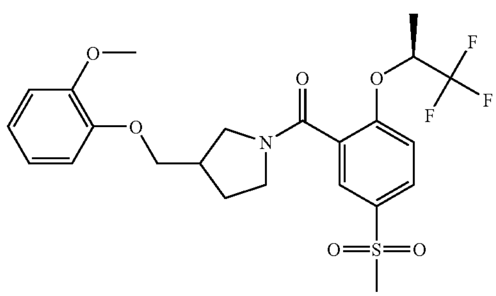 | rac-[5-Methanesulfonyl-2-((S)-2,2,2-trifluoro-1-methyl-ethoxy)-phenyl]-[3-(2-methoxy-phenoxymethyl)-pyrrolidin-1-yl]-methanone 502.0 | 2-methoxyphenol and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 501.5 |
| 39 | 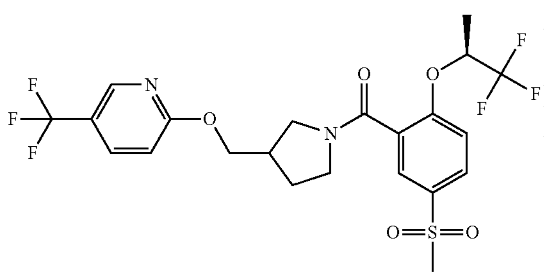 | rac-[5-Methanesulfonyl-2-((S)-2,2,2-trifluoro-1-methyl-ethoxy)-phenyl]-[3-(5-trifluoromethyl-pyridin-2-yloxymethyl)-pyrrolidin-1-yl]-methanone 541.1 | 5-Trifluoromethyl-pyridin-2-ol and rac-(3-Hydroxymethyl-pyrrolidin-1-yl)-[5-methanesulfonyl-2-((S)-2,2,2-trifluoro-1-methyl-ethoxy)-phenyl]-methanone (Example C1) | 540.4 |

Example 40 rac-[5-Methanesulfonyl-2-((S)-2,2,2-trifluoro-1-methyl-ethoxy)-phenyl]-[3-(4-trifluoromethyl-benzyloxy)-pyrrolidin-1-yl]-methanone a) rac-(3-Hydroxy-pyrrolidin-1-yl)-[5-methanesulfonyl-2-((S)-2,2,2-trifluoro-1-methyl-ethoxy)-phenyl]-methanone

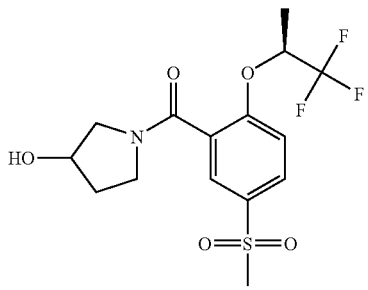

Prepared in analogy to Example C1 from 5-Methanesulfonyl-2-((S)-2,2,2-trifluoro-1-methyl-ethoxy)-benzoic acid (CAS: 845616-82-2) and rac-3-pyrrolidinol. The crude material was crystallized with dichoromethane to provide the title compound as white solid. MS (m/e): 382.3 (M+H⁺, 100%).

b) rac-[5-Methanesulfonyl-2-((S)-2,22-trifluoro-1-methyl-ethoxy)-phenyl]-[3-(4-trifluoromethyl-benzyloxy)-pyrrolidin-1-yl]-methanone

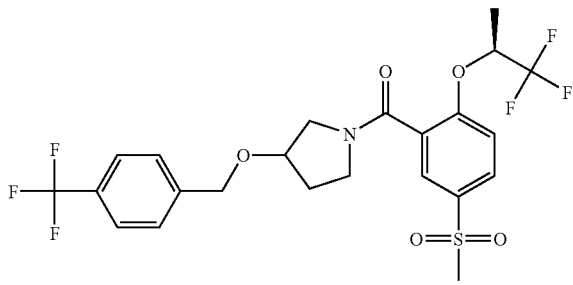

To a solution of 100 mg rac-(3-Hydroxy-pyrrolidin-1-yl)-[5-methanesulfonyl-2-((S)-2,2,2-trifluoro-1-methyl-ethoxy)-phenyl]-methanone in 1 ml DMF under argon at 0° C., was added 0.042 ml 4-(trifluoromethyl)benzyl chloride, followed by 31.2 mg sodium-tert-butoxide. The reaction mixture was stirred at room temperature for 2 days and evaporated. The residue was dissolved in ethyl acetate and was extracted 2 times with water. The organic phase was dried over Na₂SO₄ and evaporated. The residue was purified on silica gel (eluent: ethyl acetate) to yield the title compound as an oil. MS (m/e): 540.2 (M+H⁺, 100%).

The invention claimed is:

1. A compound of formula I

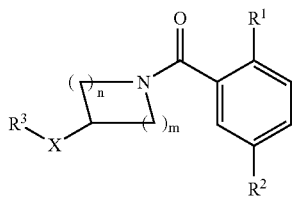

wherein
R¹ is —OR¹', or is aryl, heteroaryl, or a nonaromatic group selected from oxetanyl, tetrahydrofuranyl, tetrahydropyranyl, azetidinyl, pyrrolidinyl, piperidinyl, piperazinyl, morpholinyl and thiomorpholinyl, wherein the aryl, heteroaryl, or nonaromatic group each is unsubstituted or substituted by lower alkyl or halogen;
R¹' is lower alkyl, lower alkyl substituted by halogen, or —(CH₂)ₒ-cycloalkyl;
R² is —S(O)₂-lower alkyl, —S(O)₂NH-lower alkyl, NO₂ or CN;
R³ is aryl or heteroaryl, each of which is unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide;
X is a bond, —CH₂—, —NH—, —CH₂O— or —OCH₂—;
n is 1 m is 2; or
m is 1 n is 2; and
o is 0 or 1;
or a pharmaceutically acceptable acid addition salt thereof.

2. A compound of claim 1, wherein R³ is phenyl unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide.

3. A compound of claim 2, wherein X is a bond and R³ is phenyl, which is unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide.

4. A compound of claim 3, which compound is
rac-[5-methanesulfonyl-2-((S)-2,2,2-trifluoro-1-methyl-ethoxy)-phenyl]-[3-(4-trifluoromethyl-phenyl)-pyrrolidin-1-yl]-methanone.

5. A compound of claim 2, wherein X is —CH₂— and R³ is phenyl, which is unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide.

6. A compound of claim 5, selected from the group consisting of
rac-[5-methanesulfonyl-2-((S)-2,2,2-trifluoro-1-methyl-ethoxy)-phenyl]-[3-(4-trifluoromethyl-benzyl)-pyrrolidin-1-yl]-methanone,
rac-[5-methanesulfonyl-2-(2,2,3,3,3-pentafluoro-propoxy)-phenyl]-[3-(4-trifluoromethyl-benzyl) -pyrrolidin-1-yl]-methanone,
rac-(4'-fluoro-4-methanesulfonyl-biphenyl-2-yl)-[3-(4-trifluoromethyl-benzyl)-pyrrolidin-1-yl]-methanone,
rac-(2-cyclobutylmethoxy-5-methanesulfonyl-phenyl)-[3-(4-trifluoromethyl-benzyl) -pyrrolidin-1-yl]-methanone and
rac-(2-cyclopentyloxy-5-methanesulfonyl-phenyl)-[3-(4-trifluoromethyl-benzyl)-pyrrolidin-1-yl]-methanone.

7. A compound of claim 2, wherein X is —OCH₂— and R³ is phenyl, which is unsubstituted or substituted by one to three substituents selected from the group consisting of lower alkyl, lower alkoxy, CN, NO₂, halogen, lower alkyl substituted by halogen, lower alkoxy substituted by halogen, aryl and sulfonamide.

8. A compound of claim 7, selected from the group consisting of
rac-[3-(4-chloro-phenoxymethyl)-pyrrolidin-1-yl]-[5-methanesulfonyl-2-((S)-2,2,2-trifluoro-1-methyl-ethoxy)-phenyl]-methanone,
rac-[5-methanesulfonyl-2-((S)-2,2,2-trifluoro-1-methyl-ethoxy)-phenyl]-(3-p-tolyloxymethyl-pyrrolidin-1-yl)-methanone,
rac-[3-(biphenyl-4-yloxymethyl)-pyrrolidin-1-yl]-[5-methanesulfonyl-2-((S)-2,2,2-trifluoro-1-methyl-ethoxy)-phenyl]-methanone,
rac-4-{1-[5-methanesulfonyl-2-((S)-2,2,2-trifluoro-1-methyl-ethoxy)-benzoyl]-pyrrolidin-3-ylmethoxy}-benzonitrile,
rac-[5-methanesulfonyl-2-((S)-2,2,2-trifluoro-1-methyl-ethoxy)-phenyl]-[3-(4-nitro-phenoxymethyl)-pyrrolidin-1-yl]-methanone,
rac-[5-methanesulfonyl-2-((S)-2,2,2-trifluoro-1-methyl-ethoxy)-phenyl]-[3-(4-trifluoromethoxy-phenoxymethyl)-pyrrolidin-1-yl]-methanone,
rac-[3-(3,4-dichloro-phenoxymethyl)-pyrrolidin-1-yl]-[5-methanesulfonyl-2-((S)-2,2,2-trifluoro-1-methyl-ethoxy)-phenyl]-methanone and
rac-[5-methanesulfonyl-2-((S)-2,2,2-trifluoro-1-methyl-ethoxy)-phenyl]-[3-(3-methoxy-phenoxymethyl) -pyrrolidin-1-yl]-methanone.

9. A compound of claim 2, wherein R³ is unsubstituted phenyl.

10. A compound of claim 2, wherein $R^3$ is phenyl substituted by halogen.

11. A compound of claim 2, wherein $R^3$ is phenyl substituted by $CF_3$.

12. A compound of claim 2, wherein $R^3$ is phenyl substituted by alkoxy or alkoxy substituted by halogen.

13. A compound of claim 1, wherein X is —NH—.

14. A compound of claim 1, wherein X is —CH$_2$O—.

15. A compound of claim 1, wherein X is a bond.

16. A compound of claim 1, wherein X is —CH$_2$—.

17. A compound of claim 1, wherein X is —OCH$_2$—.

18. A compound of claim 1, wherein $R^1$ is $OR^{1'}$.

19. The compound of claim 18, wherein $R^{1'}$ is lower alkyl or lower alkyl substituted by halogen.

20. The compound of claim 1, wherein $R^1$ is a nonaromatic group selected from oxetanyl, tetrahydrofuranyl, tetrahydropyranyl, azetidinyl, pyrrolidinyl, piperidinyl, piperazinyl, morpholinyl and thiomorpholinyl.

21. The compound of claim 1, wherein $R^1$ is heteroaryl.

22. A pharmaceutical composition comprising a compound of formula I

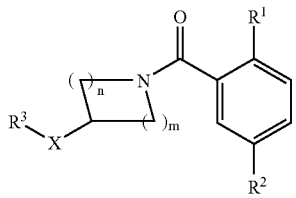

I wherein $R^1$ is —$OR^{1'}$, or is aryl, heteroaryl, or a nonaromatic group selected from oxetanyl, tetrahydrofuranyl, tetrahydropyranyl, azetidinyl, pyrrolidinyl, piperidinyl, piperazinyl, morpholinyl and thiomorpholinyl, wherein the aryl, heteroaryl, or nonaromatic group each is unsubstituted or substituted by lower alkyl or halogen;

$R^{1'}$ is lower alkyl, lower alkyl substituted by halogen, or —(CH$_2$)$_o$-cycloalkyl;

$R^2$ is —S(O)$_2$-lower alkyl, —S(O)$_2$NH-lower alkyl, NO$_2$ or CN;

$R^3$ is aryl or heteroaryl, each of which is unsubstituted or substituted by one to three substituents selected from the group consisting of lower alkyl, lower alkoxy, CN, NO$_2$, halogen, lower alkyl substituted by halogen, lower alkoxy substituted by halogen, aryl and sulfonamide;

X is a bond, —CH$_2$—, —NH—, —CH$_2$O— or —OCH$_2$—;

n is 1 m is 2; or m is 1 n is 2; and o is 0 or 1;

or a pharmaceutically acceptable acid addition salt thereof and a pharmaceutically acceptable carrier.

* * * * *